United States Patent [19]
Schneider et al.

[11] Patent Number: 5,372,999
[45] Date of Patent: Dec. 13, 1994

[54] USE OF MAGNESIUM-PYRIDOXAL-5'-PHOSPHATE-GLUTAMINATE FOR THE PREVENTION OF DISEASES WHICH RESULT FROM VASCULAR LESIONS

[75] Inventors: Werner Schneider, Koblenz; Britta Meyer, Baldham; Erich F. Elstner, Gröbenzell, all of Germany

[73] Assignee: Steigerwald Arzneimittelwerk GmbH, Darmstadt, Germany

[21] Appl. No.: 41,896

[22] Filed: Apr. 2, 1993

Related U.S. Application Data

[63] Continuation of Ser. No. 705,416, May 24, 1991, abandoned.

[30] Foreign Application Priority Data

May 25, 1990 [DE] Germany ............... 4016963

[51] Int. Cl.$^5$ ............... A61K 31/675; A61K 31/44
[52] U.S. Cl. ............... 514/81; 514/824; 514/293; 514/294
[58] Field of Search ............... 514/80, 81, 83, 304, 514/340, 293, 294

[56] References Cited

U.S. PATENT DOCUMENTS 4,925,672 5/1990 Gremm ............... 424/451

FOREIGN PATENT DOCUMENTS 2461742 7/1976 Germany .

OTHER PUBLICATIONS

CA:105(19)164785x (1986).
CA:86(16)111179k (1977).
CA:94(25) 204328p (1981).
Steadman's Medical Dictionary, Twenty-second edition p. 123 (1972).
Marshall et al., Beeinflussen die . . . medikamentose Lipidsenkung?, Apr. 1986, Therapiewoche, vol. 36, No. 15, pp. 1549–1561.
Wieland, MPPG gehort . . . medikamentosen Lipidsenkung, Feb. 1990, Fortschritte der Medizin, vol. 108, Supplement 1, pp. 52–53.

Primary Examiner—Marianne M. Cintins
Assistant Examiner—T. J. Criares
Attorney, Agent, or Firm—Sughrue, Mion, Zinn, Macpeak & Seas

[57] ABSTRACT

The invention relates to the use of magnesium-pyridoxal-5'-phosphate-glutaminate to prepare a pharmaceutical suitable for the reduction of LDL-bound peroxides and for the prophylaxis of vascular lesions resulting therefrom in the absence of hypercholesteraemia or hyperlipidaemia.

7 Claims, 4 Drawing Sheets

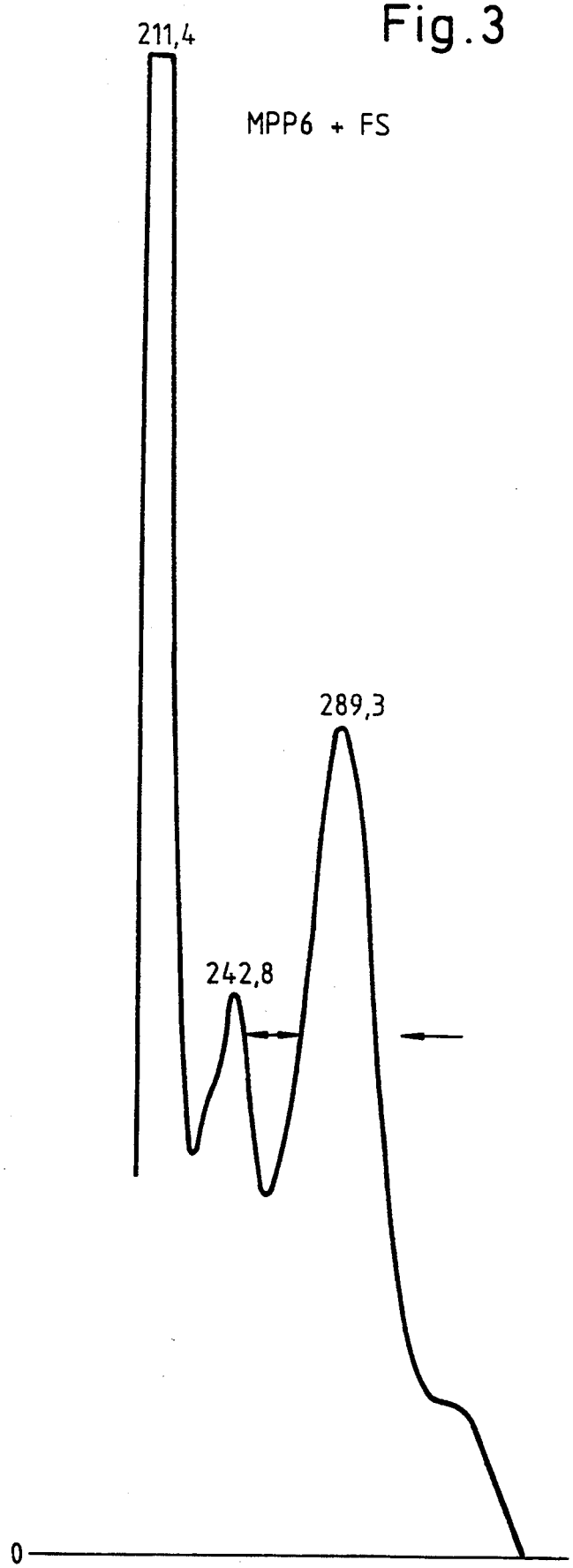

USE OF MAGNESIUM-PYRIDOXAL-5'-PHOSPHATE-GLUTAMINATE FOR THE PREVENTION OF DISEASES WHICH RESULT FROM VASCULAR LESIONS

This is a continuation of application Ser. No. 07/705,416 filed May 24, 1991, now abandoned.

FIELD OF THE INVENTION

The invention concerns the use of magnesium-pyridoxal-5'-phosphate-glutaminate to prevent diseases which are caused by LDL-bound peroxides and which result in vascular lesions.

BACKGROUND OF THE INVENTION

In the last four decades, a rapid increase could be observed in the Western industrial countries in metabolic disturbances, especially in disturbances of the fat metabolism. The main reason for this is excessive nutrition and/or too fatty foods with simultaneous lack of movement. Under these conditions, increased cholesterol and lipid values may form in the blood, which increase the risk arteriosclerotic, cardiac and peripheral vascular diseases. It is known that increased blood cholesterol levels are co-responsible for the emergence of arterial vascular sclerosis. Hypercholesteraemia is a metabolic disturbance which always accompanies hyperlipidaemia. The pathogenetically different but symptomatically similar clinical pictures of hyperlipidaemia (turbidity of the serum by chylomicrons) and of hypercholesteraemia (increase of the cholesterol content in the blood plasma to more than 200 mg %) are summarized under the collective concepts hyperlipoproteinaemia or hyperlipidaemia.

For the treatment of hypercholesteraemia, predominantly aryloxyacetic acid derivates, especially alpha-(p-chlorophenoxy)-isobutyric acid-ethylesters, as well as nicotinic acid derivatives are used.

In addition, DE-PS 24 61 742 of the applicant describes the use of pyridoxin-5'-phosphoric acid ester-glutaminates and -asparaginates for the treatment and prophylaxis of hypercholesteraemia.

Without it being necessary for the clinical picture of hypercholesteraemia or hyperlipidaemia to be present, in the case of an endangered group of persons, namely smokers, diabetics, ageing persons and those with high blood pressure or persons who are exposed to great stress, vascular lesions may occur. This is traced back to the presence of an increased concentration of peroxides in the blood, which are bonded by LDL (low density lipoprotein). These LDL-bonded peroxides cause and accelerate the formation of atheromae and arteriosclerotic plaques in the vessels and can be regarded as the cause of diabetic angiopathy. The presence of increased concentrations of peroxidizing products and their correlation with vascular lesions is described by J. M. C. Gutteridge et al. in Trends in Biochemical Sciences, April 1990, pages 129 to 135 and by D. W. Morel et al. in Journal of Lipid Research, Vol. 30, 1989, pages 1827 to 1834.

It is known that the arteriosclerotic changes in the vessels are a result of endothelial lesions, and the pathogenesis proceeds as follows: endolethelial lesion-platelet adhesion-proliferation of smooth muscle cells-lipid deposit.

The first step, the endolethial lesion, may have a plurality of causes, namely mechanical damage due to shearing forces in the case of hypertonia, chemical damage due to cholesterol in hypercholesteraemia and in particular toxic damage due to contaminants in the blood. It is assumed that the further course is almost identical with all three types of damage.

The consequence of an endothelial lesion as well as of the subsequent fat deposit between and in the cells of the arterial intima is an increased aggregation of thrombocytes, accompanied by a proliferation of smooth muscle cells, caused by the further increased inflow of lipoproteins in the connective tissue basic substance, where complex formation with glucose aminoglycans of the connective tissue and metabolic defects result on the cellular level. Then the formation of calcium in the damaged zones forms the conclusion of all the changes, which, in the final analysis, lead to a constriction of the vessels.

Tests were carried out on hypercholesteremic rabbits and rats by W. Schneider in his dissertation concluded in 1987 at the Johannes Gutenberg University of Mainz, which showed that when administering relatively high concentrations of magnesium-pyridoxal-5'-phosphate-glutaminate (MPPG), the liver and aorta lipid concentrations are reduced. But this work does not provide any indications with reference to the mechanism which initiates the vessel atheroma formation in the endangered groups of persons, so that on the basis of the results of W. Schneider, it cannot be concluded that an atheroma formation can be prevented by the elimination of the initiating contaminants in the blood.

For some time past it has been suspected that peroxides in the blood may function as the initiators of metabolic disturbances. U. P. Steinbrecher et al. describe in J. Biol. Chem., Vol. 264, No. 26, pages 15216 to 15223 (1989) the presence of oxidizingly modified LDL as well as a receptor for it. The applicant has now proven in purposeful tests that this concerns LDL-bonded peroxides. By tests made in vitro one of the mechanisms underlying toxic endothelial lesion could be clarified and it was shown that it is possible to intercept these peroxides and to render them harmless.

BRIEF DESCRIPTION OF THE DRAWINGS

FIG. 3 shows the spectrum of a solution of linolenic acid and MPPG. This spectrum has peaks at 211, 243 and 289 nm. The peak previously obtained in FIG. 1 at 232 is no longer present in FIG. 3. Instead, FIG. 3 shows two new peaks at 243 and 289 nm.

SUMMARY OF THE INVENTION

Figure 1:
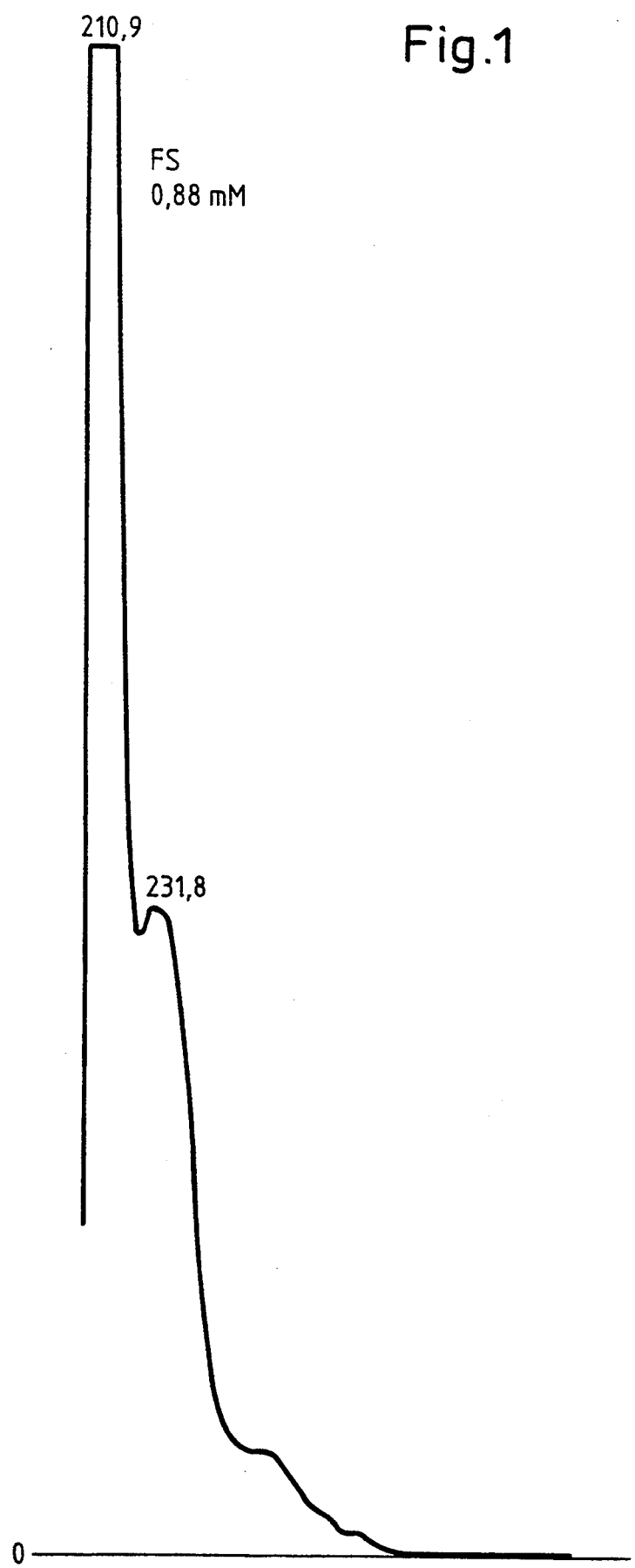
FIG. 1 shows the spectrum of linolenic acid (0.88 mM). The main peak is at 211 nm, whereas at about 232 a smaller peak is found, which points to the presence of a small percentage of oxidized linolenic acid.

The object of the invention is to provide of a pharmaceutical for the reduction of LDL-bonded peroxides in order thereby to avoid and/or to delay vascular lesions, especially the formation of atheromae or of arteriosclerotic plaques in the arterial vessels, as well as angiopathic diseases in the case of diabetics. It is especially the object of the present invention to provide a pharmaceutical also for those of the above cases where there is no diagnosis of hyperlipidaemia or hypercholesteraemia.

DETAILED DESCRIPTION OF THE INVENTION

The object above is achieved according to the invention by the use of magnesium-pyridoxal-5'-phosphate-glutaminate to prepare a pharmaceutical which is suitable for the prophylaxis of diseases caused by vascular lesions. In particular, according to the invention, atheromatosis as well as angiophatic diseases are to be prevented for an endangered group of persons, consisting of diabetics, smokers, ageing people, hypertonic persons and those under stress.

Magnesium-pyridoxal-5'-phosphate (MPPG) is a substance which previously was used to reduce increased blood fats. The substance (MPPG) is known under the tradename of Sedalipid ® and is distributed by the firm Steigerwald Arzneimittelwerk, Darmstadt. Until now it was not known that magnesium-pyridoxal-5'-phosphate-glutaminate acts as a radical interceptor in the blood and therefore is capable of preventing a chain reaction caused by lipid peroxide. On the basis of this effect as a radical interceptor, the use of MPPG is suitable for prophylaxis of vascular lesions especially in the absence of hyperlipidaemia and/or hypercholesteraemia.

MPPG is a derivate of pyridoxin and has the following formula:

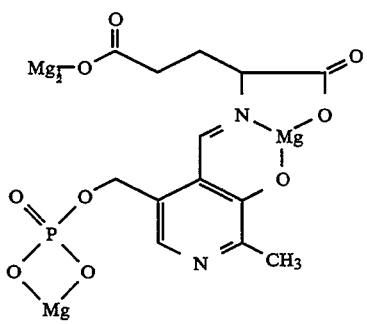

In the sense of the invention, the endangered groups of persons are particularly smokers, diabetics, those with high blood pressure as well as all persons under stress, such as top sportsmen, and ageing people.

According to the invention the above compound MPPC is administered to those endangered persons who have a high concentration of LDL-bound peroxides, however, do not suffer from the symptoms of hyperlipidaemia and/or hypercholesteraemia. These symptoms are usually determined on the basis of cholesterol levels as well as cholesterol and triglyceride levels. There exist in Europe as well as in the USA recommendations as to what may be considered normal and increased cholesterol and triglyceride levels. As to this, reference is made to the recommendations of the US National Cholesterol Education Programme (NCEP) and the guidelines provided by The European Atherosclerosis Society Study Group. In the following Tables 1 and 2 values are summarized as to what may be considered normal cholesterol and triglyceride levels, and when treatment has to be initiated:

TABLE 1

Recommendations of the US National Cholesterol Education Programme (NCEP)

| Classification | Total Cholesterol Level | Recommended follow-up |
|---|---|---|
| Desirable cholesterol | <200 mg/dl | Repeat measurement within 5 years |
| Borderline cholesterol risk | 200–239 mg/dl | If no CHD and no other risk factors: Diet information & recheck annually If definite CHD or two other CHD risk factors: Further action based on LDL level |
| High risk cholesterol | >240 mg/dl | Provide lipoprotein analysis & further action based on LDL level. |
| Desirable LDL | <130 mg/dl | — |
| Borderline LDL risk | 130–159 mg/dl | Diet treatment if CHD and two other risk factors |
| High risk LDL | 160–190 mg/dl | Diet treatment if no CHD and no other risk factors Drug and diet if CHD or two other risk factors |
|  | >190 mg/dl | Drug and diet |

TABLE 2

Guidelines from The European Atherosclerosis Society Study Group

TYPE A:
Cholesterol: 200–250 mg/dl (5.2–6.5 mmol/l)
Triglycerides: <200 mg/dl (<2.3 mmol/l)
Assess overall risk of CHD, taking into account family history of CHD, hypertension, diabetes, male sex, younger age, smoking, low HDL cholesterol eg <35 mg/dl.
Restrict food energy if overweight; give nutritional advice and correct other risk factors if present.

TYPE B:
Cholesterol: 250–300 mg/dl (6.5–7.8 mmol/l)
Triglyceride: <200 mg/dl (<2.3 mmol/l)
Assess overall risk of CHD as for type A.
Restrict food energy if overweight; prescribe lipid lowering diet and monitor response and compliance. If cholesterol remains high, consider use of lipid-lowering drug.

TYPE C:
Cholesterol: <200 mg/dl (<5.2 mmol/l)
Triglyceride: 200–500 mg/dl (2.3–5.6 mmol/l)
Seek underlying causes of hypertriglyceridaemia eg obesity, excessive alcohol intake, diuretics, beta-blockers, exogenous oestrogens, diabetes.
Restrict dietary energy if overweight; deal with underlying causes if present. Prescribe and monitor lipid-lowering diet. Monitor cholesterol and triglyceride levels.

TYPE D:
Cholesterol: 200–300 mg/dl (5.2–7.8 mmol/l)
Triglyceride: 200–500 mg/dl (2.3–5.6 mmol/l)
Assess overall risk of CHD as in Type A. Seek underlying causes of hypertriglyceridaemia as in Type C.
Restrict dietary energy if overweight; deal with underlying causes of hypertriglyceridaemia if present according to Type A or B. Prescribe and monitor lipid-lowering diet. If serum lipid response is inadequate and overall CHD risk is high, consider use of lipid-lowering drug.

Type E:
Cholesterol: >300 mg/dl (7.8 mmol/l)
and/or
Triglyceride: >500 mg/dl (5.6 mmol/l)
Consider referral to lipid clinic or to specialized physician for investigation and initiation of treatment by diet and, if necessary, drugs.

Similarly there exist published recommendations from the British Cardiac Society Working Group on Coronary Prevention, the British Hyperlipidaemia Association and the Canadian Consensus Conference on Cholesterol.

From the data shown in the above tables it is obvious that values differ slightly as to when the cholesterol content is to be considered harmful. Nevertheless, it is especially useful to realize that even below these borderlines or especially in a grey zone between still normal and increased levels, the administration of MPPG according to the invention is beneficial for those persons who belong to endangered groups having high LDL-bound peroxides.

Though no definite borderline can be given as to when a diagnosed cholesterol level is to be interpreted as a hyperlipidaemia, it is assumed that as a general guideline one may assume that approximately 240 mg/dl (according to US recommendations) or 250 mg/dl (according to EG recommendations) may be interpreted as the beginning of hyperlipidaemia. Thus, administration of MPPG according to the invention is especially considered below the above given cholesterol levels.

The inventors have carried out a number of tests to show clearly that in the endangered group of persons these high levels of LDL-bound peroxides do exist. It was also possible to show that upon addition of MPPG the detection signals indicating LDL-bound peroxides vanished. Thus, it was concluded that the application of MPPG to patients belonging to an endangered group is justified and useful.

For the increased initiation of atheroma formation, particularly in the above-named group of persons, the following mechanism is assumed, which will be documented by the tests in vitro described below:

LDL is oxidized by the reactive oxygen species (superoxide radical $O_2^-$, hydroxylradical $OH°$), especially peroxide, which are present in the blood, to form LDL peroxide. This LDL peroxide is substantially not absorbed by the macrophages, but binds on a scavenger receptor, which is located on the endothelial cells (see the literature named above by Steinbrecher et al.). In this way LDL deposits are formed on the endothelial cells which then attract further lipid deposits.

Further damage to the vessel endothelial cells is caused by the oxidation of glutathione by peroxide and/or LDL-bonded peroxide. This oxidation may lead to the death of cells, because the cell can no longer maintain its redox potential (K. Kuzuya et al. in Biochem. Biophys. Res. Comm., Vol. 163, No. 3, 1989, pages 1466 to 1472).

The following statements provide a more detailed explanation of the mechanism for the influence of MPPG on LDL-bonded peroxide. The subsequent tests show on the basis of fatty acid bonded peroxides that the latter are decomposed in the presence of MPPG and can be made harmless thereby.

The following outline reflects the assumed reaction mechanism during oxidation of a fatty acid, as is described e.g. by J. M. C Gutteridge et al. in Trends in Biochemical Sciences, April 1990, p. 130:

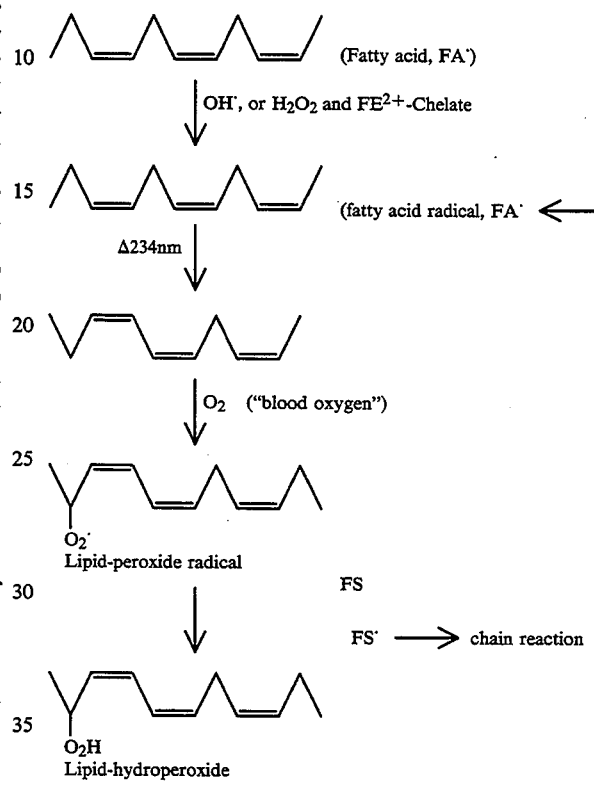

Initially there is an attack on the bridging-$CH_2$ group by a H° radical. This causes a transposition, so that conjugated double bonds are formed from the isolated double bonds. The result is the formation of a fatty acid radical, which forms in the presence of oxygen a peroxide radical. In the presence of a further fatty acid molecule, fatty acid hydroperoxide as well as a fatty acid radical are formed, whereby a chain reaction is commenced.

The reaction outline shown above can be followed at 234 nm by proof of the diene reaction.

Figure 2:
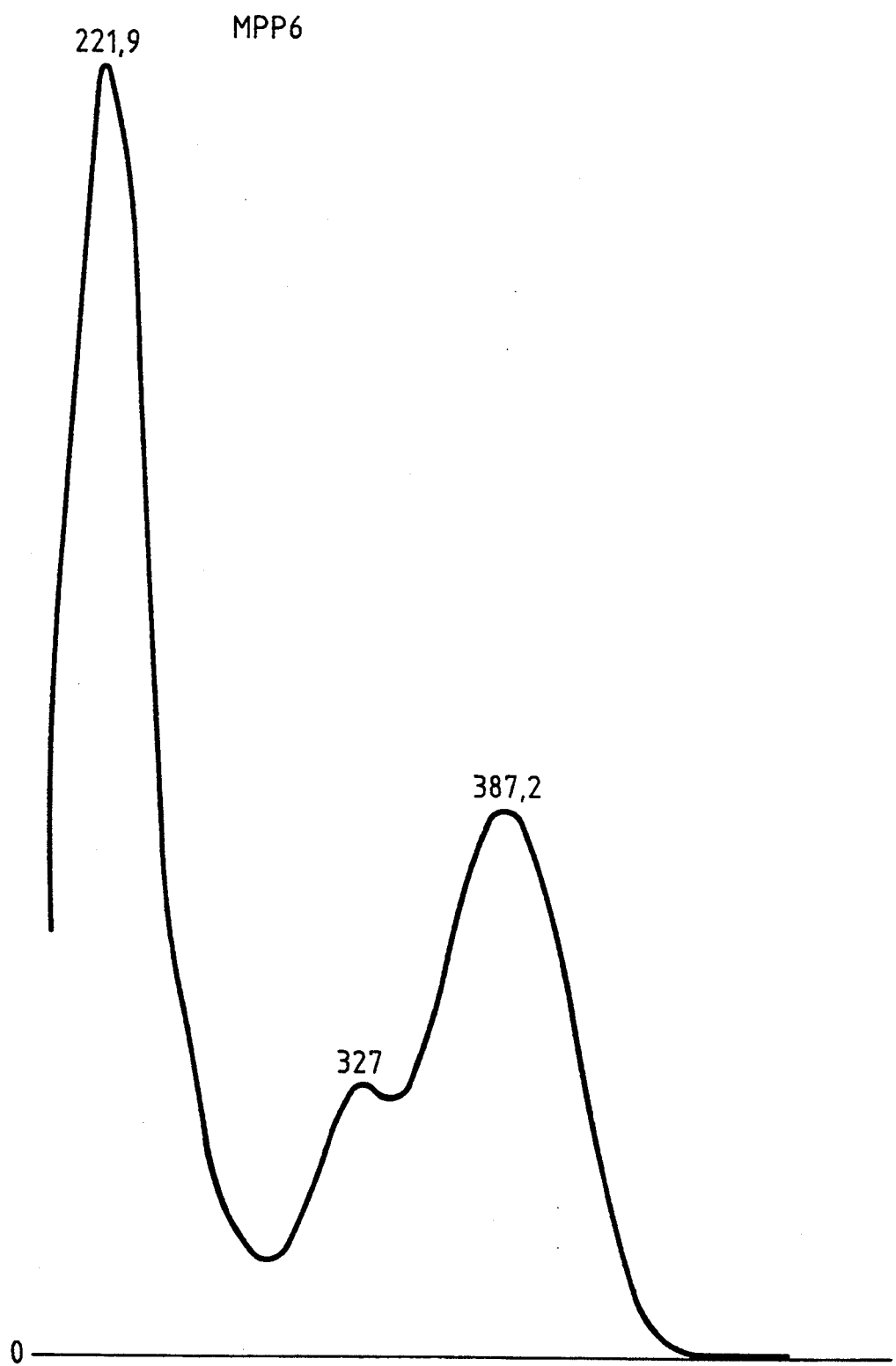
FIG. 2 reflects the spectrum of MPPG (concentration 0.125 nM) which shows peaks at 222, 327 and 387.
Figure 4A:
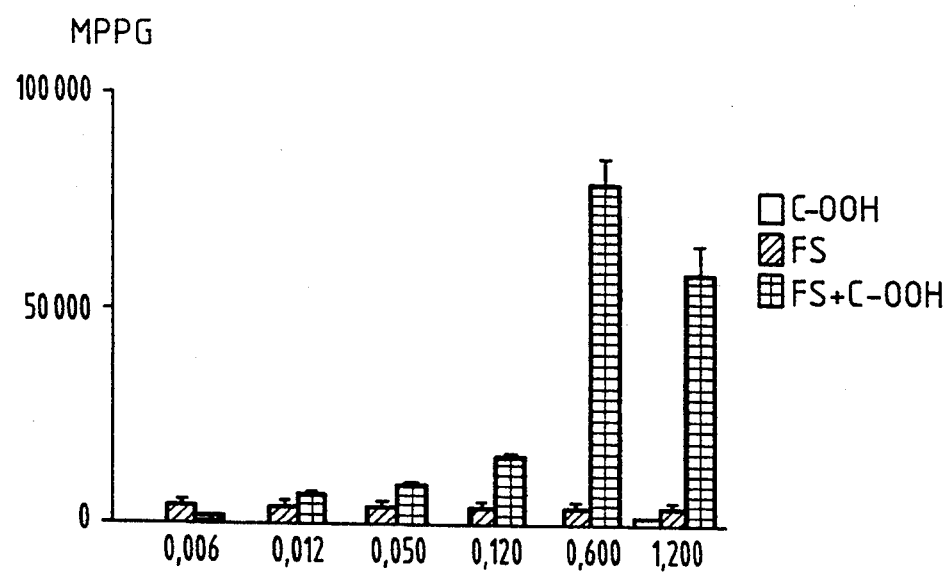
FIGS. 4a and 4b show the stimulation of ACC dissociation by MPPG or PP depending on the CumOOH concentration.
Figure 4B:
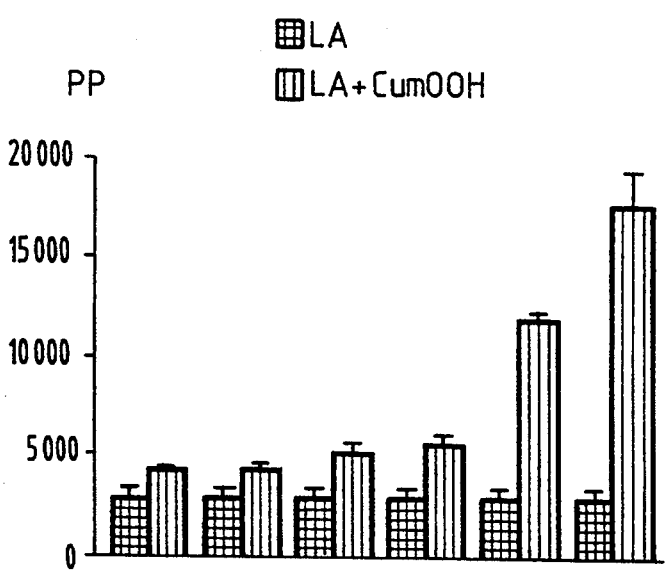

From FIGS. 1 to 3 it can be inferred that the peak for oxidized linolenic acid disappears at 232 nm (FIG. 1) by the addition of MPPG in a concentration of 0.125 mM (FIG. 3), whereby the chain reaction triggered above is interrupted and therefore the progress of the disease as well.

For the decomposition of the hydroperoxide in the presence of the substance MPPG used in accordance with the invention, the following mechanism catalyzed by manganese salt is assumed:

Proposed mechanism of the MPPG-Mn-catalysed hydroperoxide decomposition

| Magnesium-pyridoxal-5'phosphate-glutaminate | Protein-amino groups | Free biradical (N-centered) |
|---|---|---|

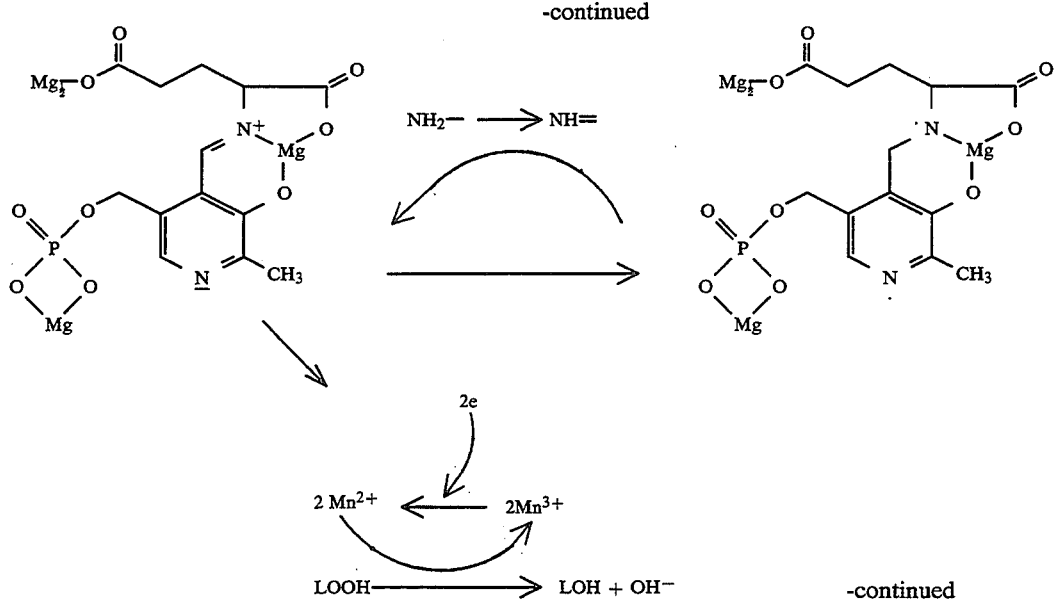

It is now possible to prove this decomposition reaction by means of the indicator substance, aminocyclopropane carboxylic acid (ACC). ACC is a basic substance occurring in nature for the formation of ethylene. The ethylene released can be quantitatively determined. The decomposition of the hydroperoxide can e.g. be followed with cumen hydroperoxide. ACC functions as an indicator. It is assumed that the reaction progresses via the amine in the pyridoxal phosphate, which causes the formation of a radical. This radical initiates decomposition of ACC into $CH_2H_4$, $CO_2$ and cyanide.

The following tests show the stimulation of ACC dissociation with MPPG in the presence of cumen hydroperoxide, depending on the cumen hydroperoxide (CumOOH) concentration. At the same time comparative tests were carried out with corresponding molar amounts of pyridoxal phosphate (PP).

Test example:

The following solutions were prepared in phosphate buffer (0.1M) pH 7.4, with different concentrations of cumen hydroperoxide.

| Batch: | Phosphate buffer 0.1M, pH 7.4 | |
|---|---|---|
| | ACC: | 1.0 mM |
| | MPPG: | 0.5 mM |
| | $Mn^{2+}$: | 0.1 mM |
| | LA: | 0.88 mM |
| | CumOOH: | 0.006–1.2 mM |
| | distilled water: | ad 2 ml |
| Tab. 1: | Stimulation of ACC dissociation by MPPG/PP by CumOOH depending on the CumOOH concentration (LA = linolenic acid; CumOOH = cumenhydroperoxide; ACC = aminocyclopropanecarboxylic acid) | |

| CumOOH-Con. (mM) | Ethylene (pMol) | | | | | |
|---|---|---|---|---|---|---|
| | 0.006 | 0.12 | 0.06 | 0.12 | 0.6 | 1.2 |
| a) MPPG | | | | | | |
| CumOOH alone | — | — | 74 ±40 | 122 ±60 | 271 ±147 | 1192 ±500 |
| LA alone | 4028 ±933 | 4028 ±933 | 4028 ±933 | 4028 ±933 | 4028 ±933 | 4028 ±933 |
| theoret. Σ | 4028 | 4028 | 4102 | 4150 | 4299 | 5219 |
| LA + CumOOH | 1014 | 6926 ±407 | 9655 ±471 | 16059 ±565 | 79079 ±5672 | 57894 ±6768 |
| Stimulation (%) | — | 72.0 | 139.7 | 298.7 | 1863.3 | 1337.4 |
| b) PP | | | | | | |
| CumOOH alone | — | — | — | — | — | — |
| LA (= theoret. Σ) | 2972 ±439 | 2972 ±439 | 2972 ±439 | 2972 ±439 | 2972 ±439 | 2972 ±439 |
| LA + CumOOH | 4319 ±173 | 4394 ±250 | 5247 ±540 | 5635 ±533 | 11972 ±425 | 17695 ±1827 |
| Stimulation (%) | 45.3 | 47.8 | 76.5 | 89.6 | 302.8 | 495.3 |

In the ACC dissociation with pyridoxal phosphate, a measurable release of ethylene was observed, in contrast to MPPG, in the lower concentration range which was used for cumenhydroperoxide (0.006 mM). At 0.12 nM CumOOH, in the presence of MPPG, a stimulation of the ACC dissociation of 70% was found. With CumOOH concentrations of 0.6 mM and 1.2 mM, clearly higher stimulation effects were measured in the presence of MPPG, by comparison with PP.

We claim:

1. A therapeutic method for reducing LDL-bound peroxides and for the prophylaxis of atheromatosis or angiopathic disease resulting therefrom in the absence of hypercholesteremia or hyperlipidemia comprising administering to patients in need of treatment, a therapeutically effective amount of magnesium-pyridoxal-5′-phosphate-glutaminate, a manganese salt, and a pharmaceutically acceptable diluent, excipient or binder.

2. The method of claim 1, wherein said patients are diabetics, smokers, aged people, people with high blood pressure or people under stress.

3. The method of claim 1, wherein said method is for the prophylaxis of atheromatosis.

4. The method of claim 1, wherein said method is for the prophylaxis of angiopathic disease.

5. The method of claim 2, wherein said method is for the prophylaxis of atheromatosis.

6. The method of claim 2, wherein said method is for the prophylaxis of angiopathic disease.

7. A composition for reducing LDL-bound peroxides and for the prophylaxis of atheromatosis or angiopathic disease resulting therefrom in the absence of hypercholesteremia or hyperlipidemia comprising a therapeutically effective amount of magnesium-pyridoxal-5′-phosphate-glutaminate, a manganese salt, and a pharmaceutically acceptable diluent, excipient or binder.

* * * * *